(12) United States Patent
Tenconi et al.

(10) Patent No.: US 9,931,948 B2
(45) Date of Patent: Apr. 3, 2018

(54) ELECTRICAL PULSE GENERATOR OF HIGH CURRENT, POWER AND ENERGY

(71) Applicant: Energy Technology S.r.l., Valsamoggia (Bologna) (IT)

(72) Inventors: Sandro Maria Tenconi, Milan (IT); Giuseppe Taddia, Pieve di Cento (IT)

(73) Assignee: ENERGY TECHNOLOGY S.R.L., Valsamoggia (IT)

( * ) Notice: Subject to any disclaimer, the term of this patent is extended or adjusted under 35 U.S.C. 154(b) by 0 days.

(21) Appl. No.: 15/628,129

(22) Filed: Jun. 20, 2017

(65) Prior Publication Data
US 2017/0368950 A1  Dec. 28, 2017

(30) Foreign Application Priority Data

Jun. 22, 2016  (IT) .......................... 102016000064899

(51) Int. Cl.
| | |
|---|---|
| G05F 1/00 | (2006.01) |
| H02M 7/00 | (2006.01) |
| H02M 7/521 | (2006.01) |
| B60L 11/18 | (2006.01) |
| H02M 3/335 | (2006.01) |
| H02M 3/158 | (2006.01) |
| H02M 3/24 | (2006.01) |
| H02M 3/07 | (2006.01) |
| A61N 1/02 | (2006.01) |

(52) U.S. Cl.
CPC .......... *B60L 11/1805* (2013.01); *A61N 1/025* (2013.01); *H02M 3/07* (2013.01); *H02M 3/158* (2013.01); *H02M 3/24* (2013.01); *H02M 3/33576* (2013.01)

(58) Field of Classification Search
CPC .......................... H02M 7/5152; H02M 7/5155
USPC .................. 323/242, 288; 363/124, 135, 136
See application file for complete search history.

(56) References Cited

U.S. PATENT DOCUMENTS

| | | | |
|---|---|---|---|
| 3,777,176 A | 12/1973 | Praeg | |
| 6,654,261 B2 * | 11/2003 | Welches ................ | H02M 1/126 363/131 |
| 2007/0108956 A1 * | 5/2007 | Steigerwald ............ | H01F 6/006 323/288 |

(Continued)

FOREIGN PATENT DOCUMENTS

WO  WO9701213 A1  1/1997

OTHER PUBLICATIONS

Italian Search Report dated Feb. 28, 2017 for counterpart Italian Application No. IT UA20164604.

*Primary Examiner* — Gary Nash
(74) *Attorney, Agent, or Firm* — Shuttleworth & Ingersoll, PLC; Timothy J. Klima

(57) ABSTRACT

An electrical pulse generator for ohmic-inductive loads with a capacitive module in which a primary capacitor is charged by a first generator for generating voltage pulses, with high capacity and high voltage, on an ohmic-inductive load. In the capacitive module there is also a secondary capacitor or supercapacitor with a very high capacity, charged by a second generator designed to continuously supply voltage to the load. An electronic splitter, or Chopper is interposed between the capacitive module and the load which splits the voltage supplied by the capacitive module according to modulated high frequency pulses, in such a way that the value of the voltage supplied to the load is constant.

12 Claims, 11 Drawing Sheets

(56) References Cited

U.S. PATENT DOCUMENTS

2014/0177299 A1\* 6/2014 Wang ...................... H02J 3/382
                                                    363/65

\* cited by examiner

ELECTRICAL PULSE GENERATOR OF HIGH CURRENT, POWER AND ENERGY

This application claims priority to Italian Patent Application IT102016000064899 filed Jun. 22, 2016, the entirety of which is incorporated by reference herein.

This invention relates to industrial and research applications in which the supply of energy in large quantities is requested, in the form of high current pulses, used to create high intensity and rapidly variable magnetic fields, by supplying inductors with high intensity currents (in the order of kA's) for times in the order of seconds.

These applications also require that the value of the steady state current is reached in times in the order of milliseconds or tens of milliseconds, therefore with high value current derivatives, and that the steady state value is maintained for much longer times.

This translates into the need on the one hand of initially supplying the ohmic-inductive loads with high voltages (and therefore high powers, in the order even of tens of MW) and on the other of hand of continuing the supply of the same loads with lower average voltages (and hence smaller powers in the order of tens or hundreds of kW).

These requirements are currently met with the use of controlled rectifiers of extremely large currents and high voltages (and hence extremely large power) which supply the above-mentioned loads and which derive the power from the mains in high voltage or from alternators which act as mechanical flywheels. As an alternative to the controlled rectifiers, uncontrolled rectifiers are also used (with diodes) coupled with power converters as splitters (choppers) or inverters.

Recently, instead of deriving the energy from the mains or from large flywheels, the use has been proposed of supercapacitors, coupled with power converters such as splitters (choppers) or inverters.

However, this system has the drawback, however, that the large capacity of storing energy of the supercapacitors is coupled with a very limited voltage (a few hundred volts) even in the case of a very large number of cells in series, and a limited maximum current (both effective and peak).

For this reason, the use of supercapacitors, whilst allowing high currents to be obtained for long periods, does not allow high current derivatives to be obtained on loads with significant inductance.

Lastly, the permissible alternating current in the supercapacitors is strongly dependent on the frequency, and it reduces with the increase in the frequency beyond a few Hz, so it is necessary to interpose an adequate low-pass filter between splitters or inverters and supercapacitors.

The aim of this invention is to provide a current pulse generator for ohmic-inductive loads which is able to provide an initial current pulse which reaches the maximum value in an extremely short period of time and subsequently a pulse of greater duration with substantially constant "steady state" current, which does not, therefore, determine a decrease in the voltage at the terminals of the load itself.

A further aim of this invention is to provide a pulse generator with which it is possible to carry out a recovery, at least partial, of the energy stored in the ohmic-inductive load, in order to reuse it for supplying the load itself.

An aim of this invention is also to provide a circuit for the above-mentioned generator in which are prevented negative effects determined by any alternating components produced by this circuit as a result of an adjustment of the PWM type.

The above-mentioned aims are achieved by an electrical pulse generator for ohmic-inductive loads, comprising a power supply module provided for supplying a pulse voltage with duration $\Delta t$ at the terminals of an ohmic-inductive load, and a module which is able to maintain a constant steady state current through the ohmic-inductive load for predetermined periods of time with a much longer duration than that of the pulses of duration $\Delta t$ even in terms of several orders of magnitude, the generator comprising:

a capacitive module charged for the supply of a voltage pulse having a predetermined value and a constant operation voltage higher than a voltage necessary to circulate a current circulate through the ohmic-inductive load;

a regulation module designed to split the voltage supplied by the capacitive module according to high-frequency pulses, wherein:

the capacitive module comprises one or more primary capacitors (preferably of traditional type) for generating voltage pulses, with high capacity and high voltage, charged by a first generator to the voltage to deliver energy so as to provide a voltage pulse having a corresponding voltage value;

and wherein the capacitive module comprises amongst other things one or more secondary high capacity capacitors, generally supercapacitor modules, connected in parallel, and charged by a second generator at a voltage lower than the previous one, to continuously supply voltage.

The features of the invention which do not emerge from the above are made clear in the following description, which should be considered with reference to the accompanying drawing, in which:

FIG. 1 illustrates a first configuration of a circuit of the electrical pulse generator for ohmic-inductive electrical loads, designed for industrial or research applications, for which magnetic fields of high intensity and quickly variable must be generated.

Figure 1:
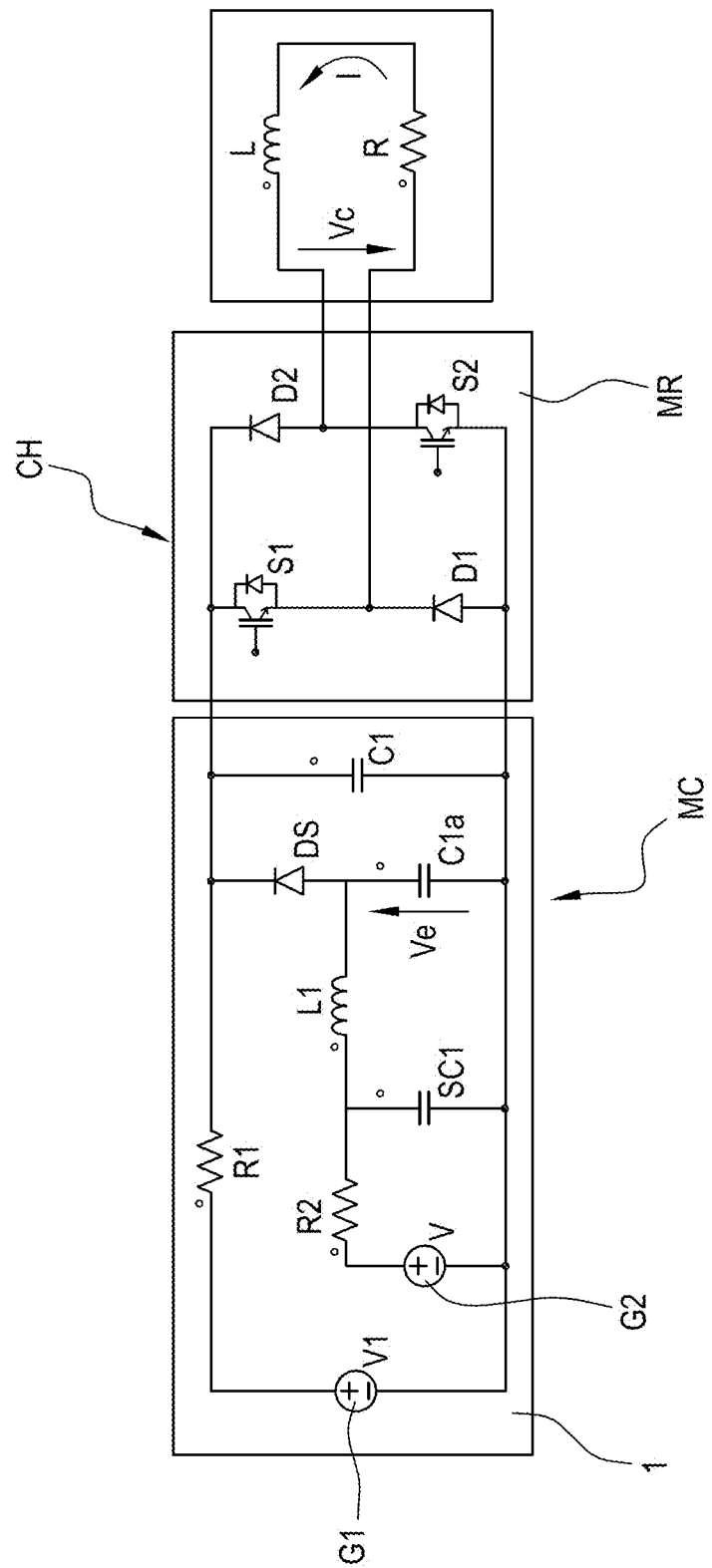
FIG. 1 illustrates a first configuration of the circuit which forms part of the pulse generator according to this invention.

The circuit of FIG. 1 comprises a power supply module 1 designed to provide initially a pulse voltage V1 with a duration $\Delta t$ at the terminals of an ohmic-inductive load LR.

Subsequently, the power supply module 1 must provide a substantially constant voltage Vc provided for maintaining a constant steady state current I through the load LR for much longer periods of time.

For this purpose, the power supply module 1 comprises a capacitive module MC in which one or more primary capacitors, indicated in its entirety by C1, are charged by a first generator G1 which delivers the desired voltage V1.

The capacitor C1 can be preferably made with several capacitors in parallel, which are inserted or removed off-load by suitable circuit breakers.

By applying the voltage at the terminals of the capacitor C1 to the ohmic-inductive load LR, the high voltage which is immediately applied on the load causes a current pulse I with extremely steep gradient, which moves rapidly to the desired or necessary value.

In practice, the initial current pulse requested is provided with the use of a capacitor C1, or, rather, capacitors, charged to a voltage value adequate for the inductance L of the charge and the derivative of the desired current I.

Reference will often be made below to a single primary capacitor C1, but it is understood that it may in reality correspond to a battery of capacitors in parallel, in order to obtain the capacity adequate to the energy which must be stored.

The relationship between the quantities in play is given by the following formulae:

$$CV^2 > LI^2$$

and $$\Delta t \approx T/4 = \pi/2(LC)^{1/2}$$

The first expresses the fact that the energy in the capacitor C1 must be higher than the energy in the inductance L at the steady state current.

The second formula puts in relation the values of the capacity of the main capacitor C1 and the inductance of the load so that the transfer of energy from the main capacitor to the inductor occurs in a time $\Delta t$ which is not greater than that desired. In effect, the capacity of the resulting circuit (in practice C1) determines, together with the inductance of the load, the discharge time of the capacitor C1 and that of any recovery at the end of the pulse.

It follows that:

$$V > I(L/C)^{1/2}$$

and $$C \leq (2\Delta t/\pi)^2/L$$

Thus, for example, if the load consists of an inductor with inductance L=0.5 mH, and resistance R=4 mΩ, with a desired current I=25 kA and for an initial pulse time $\Delta t$=10 ms, C≤80 mF is obtained.

If a capacitor SC1 of 50 mF is selected, V>2500 V, resulting in the derivative of the initial current I being 5 A/µs. The energy in the capacitor C is therefore approximately 160 kJ.

The capacitive module MC must also provide the entire energy needed to circulate a current I through the ohmic-inductive load LR for a desired time (much longer than $\Delta t$), applying obviously a constant operating voltage Ve which is higher than the voltage Vc=R*I necessary.

More in detail, the capacitive module MC contains, as well as other components, one or more secondary capacitors SC1, often indicated below with the term "secondary capacitor" or supercapacitor, for simplicity, with a high capacity, connected in parallel, and charged by a second generator G2 which supplies the voltage Ve.

The function of the secondary capacitor or supercapacitor SC1 is to provide the voltage continuously for the pulse after the initial one and with a greater duration.

The voltage Ve is less than the voltage V1 and to prevent that the primary capacitor C1 discharges on the supercapacitor SC1, between the positive terminals of them there is interposed a diode DS, in series with the primary capacitor C1. For this purpose, the diode DS has reverse blocking voltage VRRM>V1.

In order to maintain the voltage Vc applied to the load constantly over time, the voltage Ve has been fixed to a value greater than the voltage Vc and a regulating module MR has been inserted between the load and the capacitive module MC which is able to split the voltage Ve supplied by the capacitive module MC.

Advantageously, the capacitive module MC is contained inside the power supply module 1 and together with the regulation module MR they are integrated in a single electronic circuit.

The method used for splitting the voltage is that of supplying it in high frequency pulses (from several hundreds of Hz to a few kHz) and, if necessary, which can be modulated in amplitude and/or frequency (PWM). The amplitude of the pulses is increased gradually as the voltage at the terminals of the supercapacitor SC1 tends to decrease, in such a way that in the unit of time the average voltage Vc applied to the load is constant, as is the current I which passes through the load LR.

Supplying the subsequent voltage Vc to the initial pulse requires a power P>R12, which represents the nominal power dissipated by the load LR under steady-state conditions.

In our example, in order to keep the current at 25 kA a voltage of not less than 100 V is necessary, that is to say, a power P>2.5 mW, for example for 4 seconds (thus a total energy of 10 MJ).

The system of supercapacitors in parallel is, in this specific case, characterised by operating voltages of not greater than 170 V and currents in the order of kA for each supercapacitor.

The regulating module MR consists of an electronic splitter, better known as a Chopper CH, in this case with two quadrants.

The Chopper CH allows regulation of the value of the voltage Ve supplied by the capacitive module MC applying at the terminals of the load LR a constant voltage Vc, obtaining this result by varying the intermittence factor (referred to as duty cycle) inversely corresponding to the reduction of the voltage Ve supplied by the capacitive module MC, caused by the dispensing of energy by the latter.

More in detail, the Chopper CH with two quadrants comprises two semiconductor switches S1, S2 and two diodes D1, D2 connected alternately in series between the terminals of the load LR and those of the power supply module 1.

The operation of the generator is performed as illustrated below.

By enabling the two semiconductor switches S1 and S2, the capacitor C1, previously charged by the first generator G1, transfers its energy to the inductor L (except for the dissipative losses), which are discharged.

As already mentioned, the voltage pulse causes a current I with an extremely steep rise, which reaches a predetermined value in the time required and holds it for a few milliseconds.

When the current in the load reaches the desired value, at the end of the interval time of duration $\Delta t$, the voltage on C1 is now close to the value of Ve, and it would tend to zero, and also reverse due to the effect of the reflow of the current due to the energy stored in the inductive circuit of the load.

The diode DS at this point enters into conduction and, coupling the voltage at the terminals of C1 to Ve of the supercapacitors SC1, in effect locks the outflow of the current I from C1 towards the load.

On the other hand, the current of the load coming from C1 is almost completely transferred to the supercapacitors SC1.

As explained above, the activation times of the two semiconductor switches S1 and S2 is controlled in such a way as to determine the splitting of the voltage Ve, and the voltage at the terminals of the load LR is kept constant, as well as the current I passing through it.

In practice, the value of the current I is adjusted to the requested value by varying the intermittence factor of the two semiconductor switches S1 and S2 and varying, consequently, the average value of the voltage Vc applied to the load LR.

At the end of the pulse the two switches S1 and S2 are disabled.

The current in the load must flow towards the primary capacitor C1 through the diodes D1 and D2, which allow the reflow of the current I towards the capacitor C1, recovering in this way part of the energy previously supplied to the load LR.

The magnetic energy in the inductance L is thus recovered in the primary capacitor C1, the voltage of which increases to values close to the initial values (that is to say, to V1).

The semiconductor switches of the Chopper S1, S2 have an inhibiting voltage VDRM always >V1, as well as the diodes D1, D2 and DS.

Both the first G1 and second G2 generators are uncoupled from the capacitor C1 and from the supercapacitors SC1 by resistors R1, R2 or by other components.

During the time of inhibiting the semiconductor switches S1, S2, the second generator G2 performs the recharging of supercapacitors SC1.

Moreover, since between one pulse and the other there is in general several minutes, the power requested from the first G1 and second G2 generators to recharge the primary capacitor C1 and the supercapacitors SC1 is generally very limited.

Figure 2:
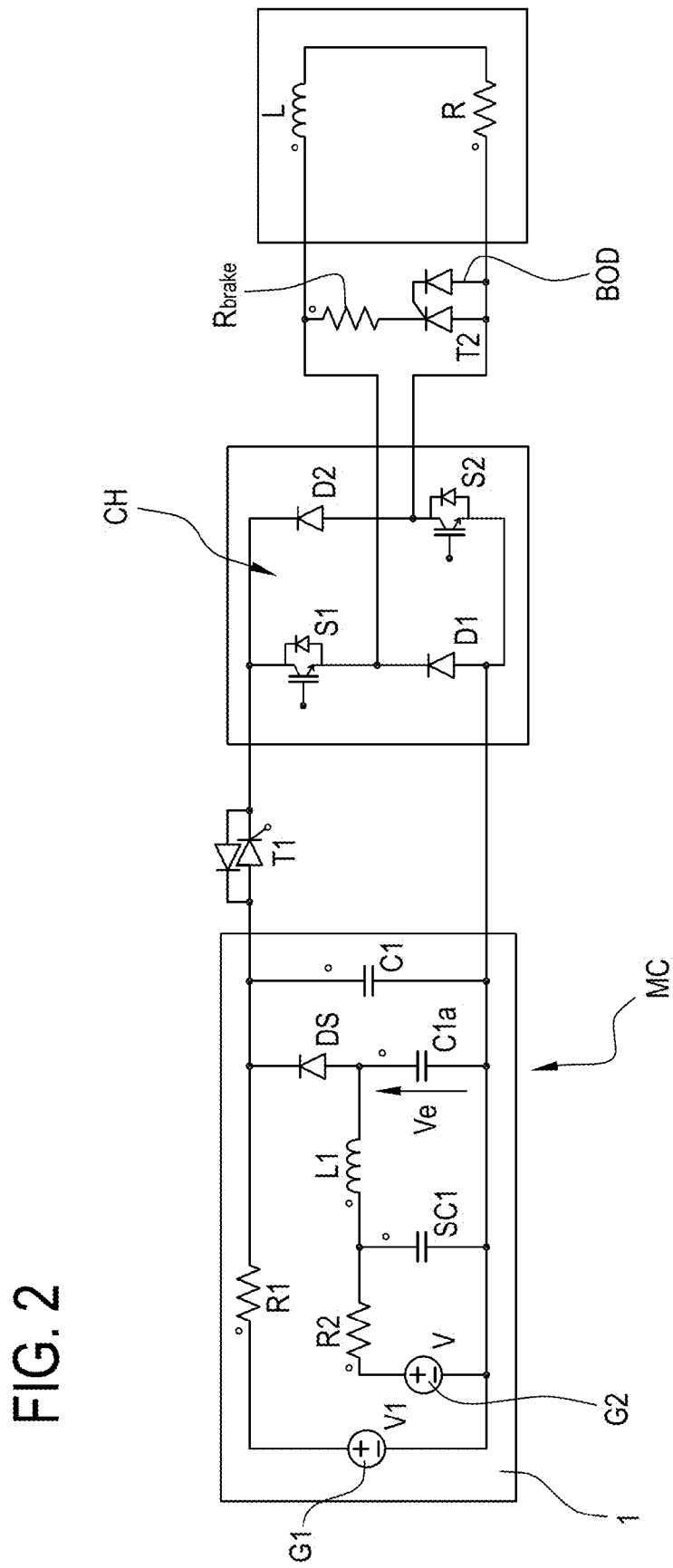
FIG. 2 illustrates a second configuration of the circuit of the generator according to this invention.

FIG. 2 shows a second configuration of the electronic circuit which constitutes the pulse generator according to this invention.

In this case, the semiconductor switches S1 and S2 have a value VDRM≤V1, which may, for example, occur if the semiconductor switches S1 and S2 must have high switching speed and frequency. The diodes DS, D1 and D2, must, on the other hand, have a reverse voltage VRRM>V1, if necessary placing two diodes in series.

In this configuration a first thyristor T1 has been added in locked position, and a terminal has been interposed which from the power supply module is connected to the splitter or Chopper CH.

Moreover, there is a second thyristor T2 in parallel with the load LR with in series a braking resistance Rbrake. In parallel to the second thyristor T2 there a Breakover diode BOD.

After the semiconductor switches S1 and S2 have been both enabled, the first thyristor T1 is triggered and the voltage on C1 is thus applied to the terminals of the load LR.

At the end of the rising ramp, the voltage of C1 falls below the value of Ve and the supercapacitors SC1 intervene to maintain the current in the load LR at the desired level.

At the end of the pulse, the semiconductor switches S1 and S2 are disabled and the energy reflows into the primary capacitor C1.

The voltage at the terminals of the capacitor C1 increases, but only to a voltage less than the value VDRM of the semiconductor switches S1 and S2.

The thyristor T2 now intervenes, triggered by the Breakover diode BOD, which inserts the braking resistance Rbrake.

The fall in the value of the current intensity will be exponential from this moment onwards, and hence less fast than the rise.

If, on the other hand, the time of falling of the intensity value of the current must be equal to that of rising (therefore excluding the use of the braking resistance), it will be necessary to use for the semiconductors switches S1 and S2 two components in series, which, however, switch, at the start and at the end of the pulse.

The voltage in this case is zero at the terminals of the semiconductor switches (ZVS=Zero Voltage Switching), whilst during the flat top, the long pulse with constant voltage Vc, since the voltage Ve<VDRM for each semiconductor of the semiconductor switches S1 and S2, the switching could be carried out by only one of the components in series, whilst the other remains always enabled.

Figure 3:
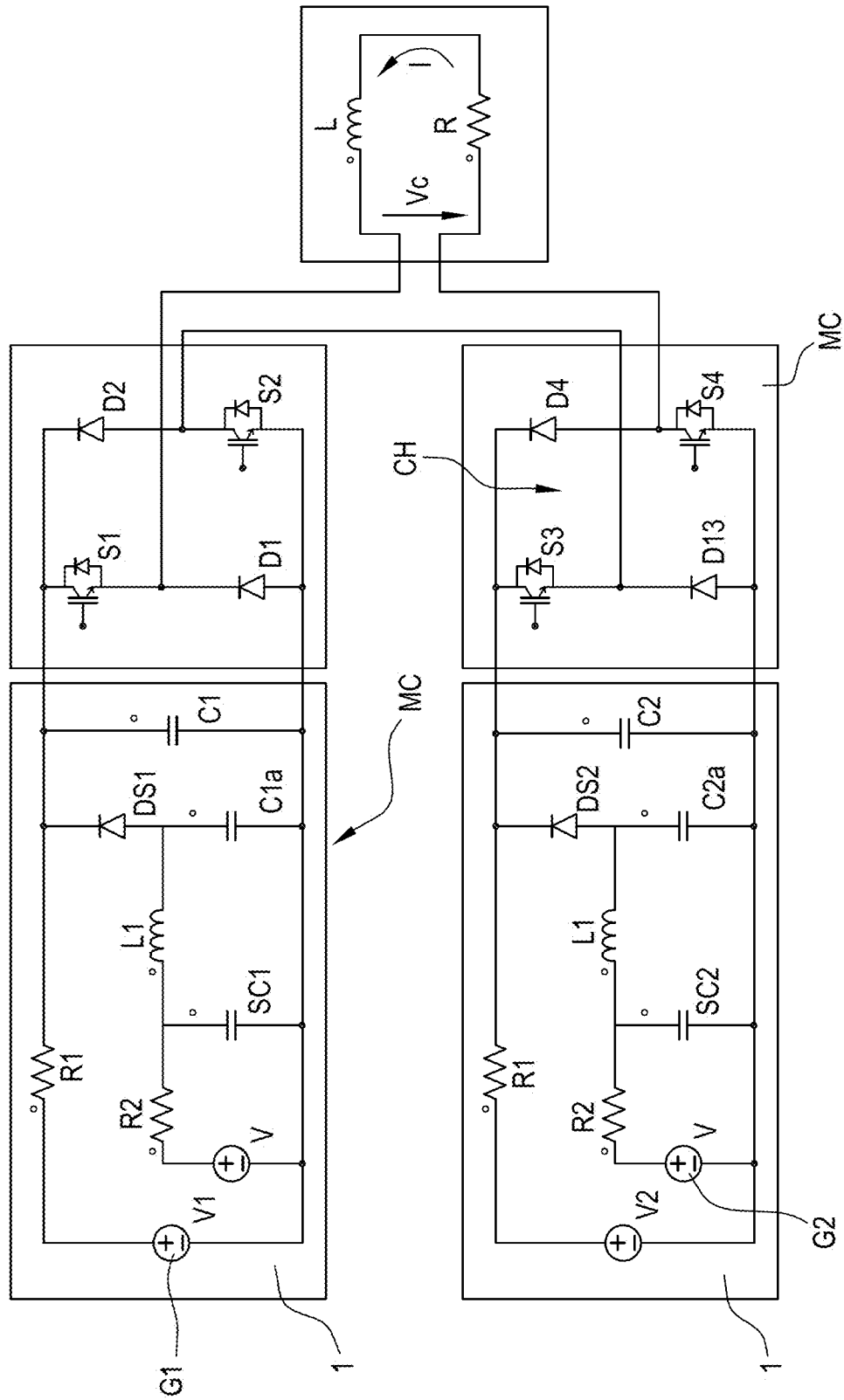
FIG. 3 illustrates a third configuration of the circuit of the pulse generator according to this invention.

FIG. 3 shows a third configuration of the modular circuit, again in the case in which the voltage required to determine a rapid rising of the value of the current in the load LR is greater than the values of the voltages VDRM and VRRM available for the semiconductor switches S1, S2, and for the diodes Ds, D1 and D2.

This configuration may also be adopted in an alternative to that illustrated in FIG. 2 and can be replicated even with a number of levels greater than 2.

In this third configuration, two or more power supply modules 1 are respectively connected to two or more voltage splitters or Choppers CH, which are in turn connected in series and applied to the load LR.

This allows greater powers to be reached for powering the load LR.

Figure 4:
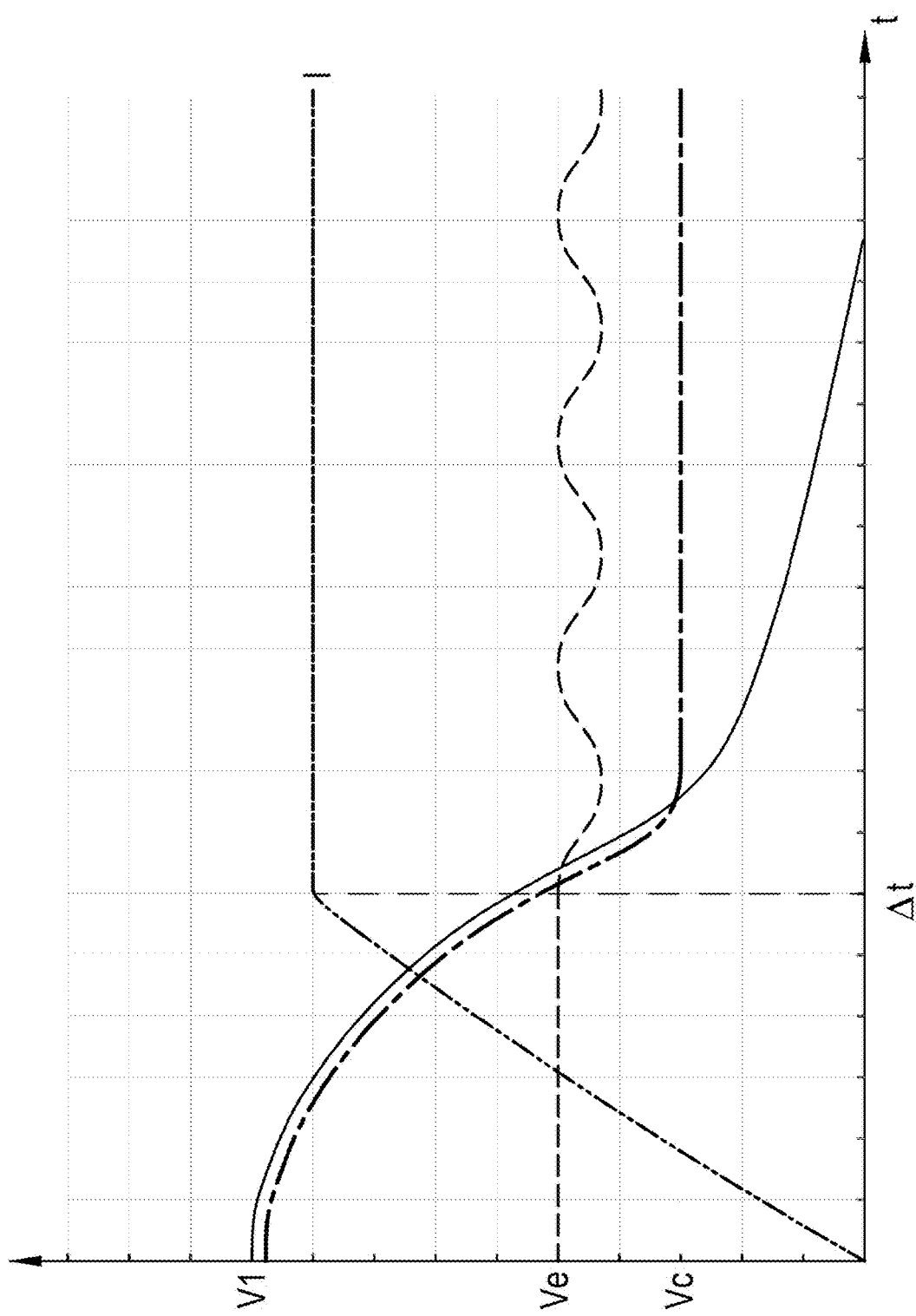
FIG. 4 illustrates a diagram in which are schematically shown the possible trends of the currents and voltages with respect to time.

Lastly, FIG. 4 shows a diagram illustrating the trend of the current I which passes through the load LR with variations in the conditions of the voltage Vc and of the voltages V1 and V2, relative to time.

As can be seen, the rising of the current I is very steep given the value V1 almost immediately maximum but rapidly falling due to the discharge of the primary capacitor C1.

When the voltage V1 decreases below the value of the voltage Ve the latter voltage is applied to the load LR modulating it in such a way as to keep the current I at the value reached for the entire duration of the pulse.

As may be inferred from above, the aims which were initially preset have been achieved with this invention.

When the secondary capacitors, or supercapacitors, provide the steady state voltage, with a discharging phase after the flow of current towards the load LR, there is no detectable reduction in the voltage at their terminals, and therefore no reduction in the current through the load LR.

The average voltage Vc applied to the ohmic-inductive load LR is therefore maintained constant, and consequently the current I passing through it, for the entire duration of the pulse.

The current pulse generator according to this invention is able to provide an initial current pulse which reaches the maximum value in an extremely short period of time and subsequently a pulse of greater duration with constant "steady state" current, which does not determine a decrease in the voltage at the terminals of the load itself.

Moreover, the pulse generator according to the invention may carry out at least a partial recovery of the energy stored in the ohmic-inductive load LR, carrying it to the primary capacitor C1 and then to the secondary capacitor or supercapacitors SC1, in order to reuse it to supply the load LR.

The LC filter provided in the capacitive module MC prevents the negative effects determined by the alternating components produced by the regulation system WMP actuated by the Chopper CH.

It should be noted that the reference C1a denotes a normal capacitor (which, therefore, is not a supercapacitor). the component is optional in the circuit.

When the diode DS1 couples, thus transferring the majority of the continuous current component from C1 to SC1, the diode becomes functionally a short circuit, and C1, together with L1, to all intents and purposes performs the function of low-pass filter.

Figure 5:
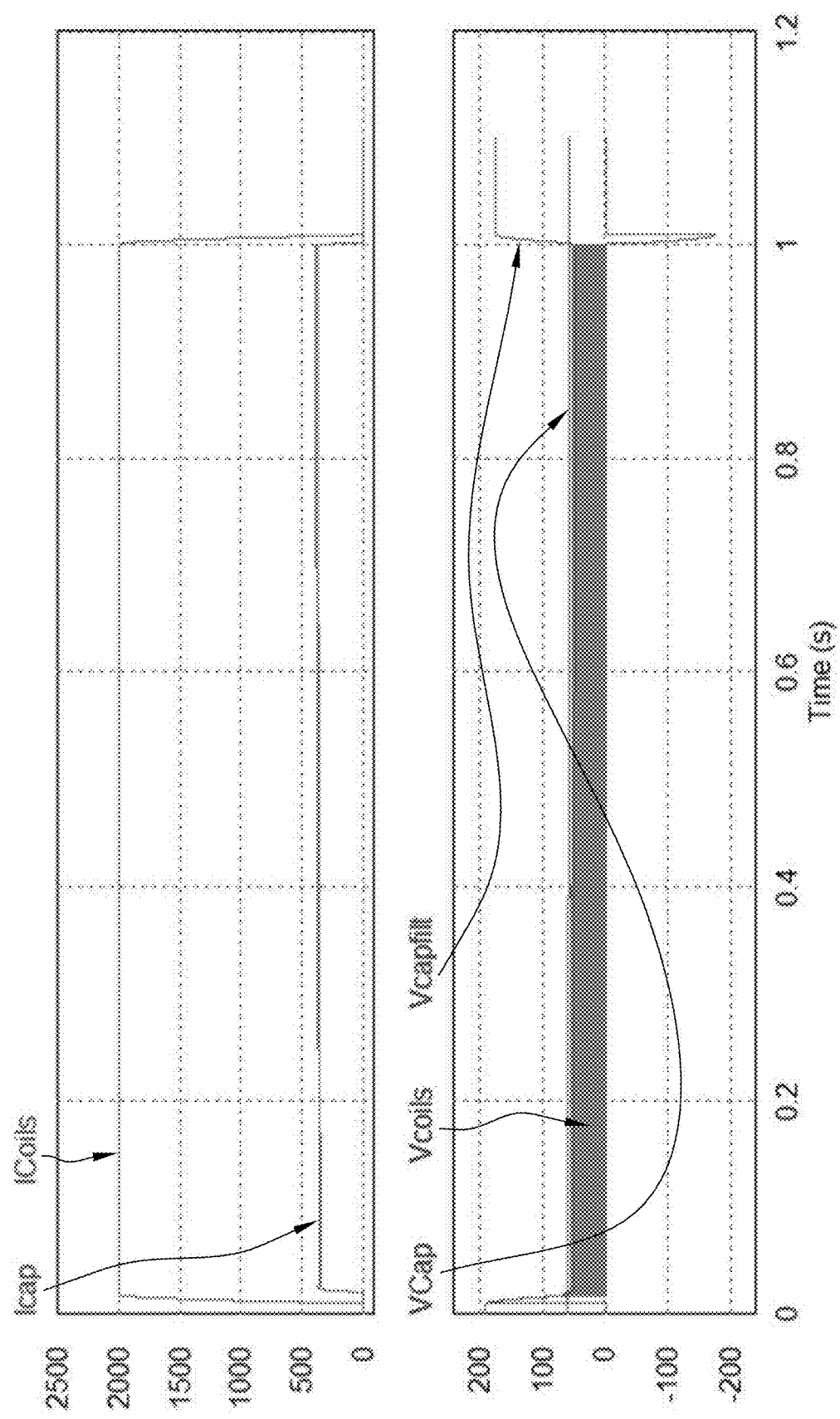
FIG. 5 illustrates a diagram relative to a pulse.
Figure 6:
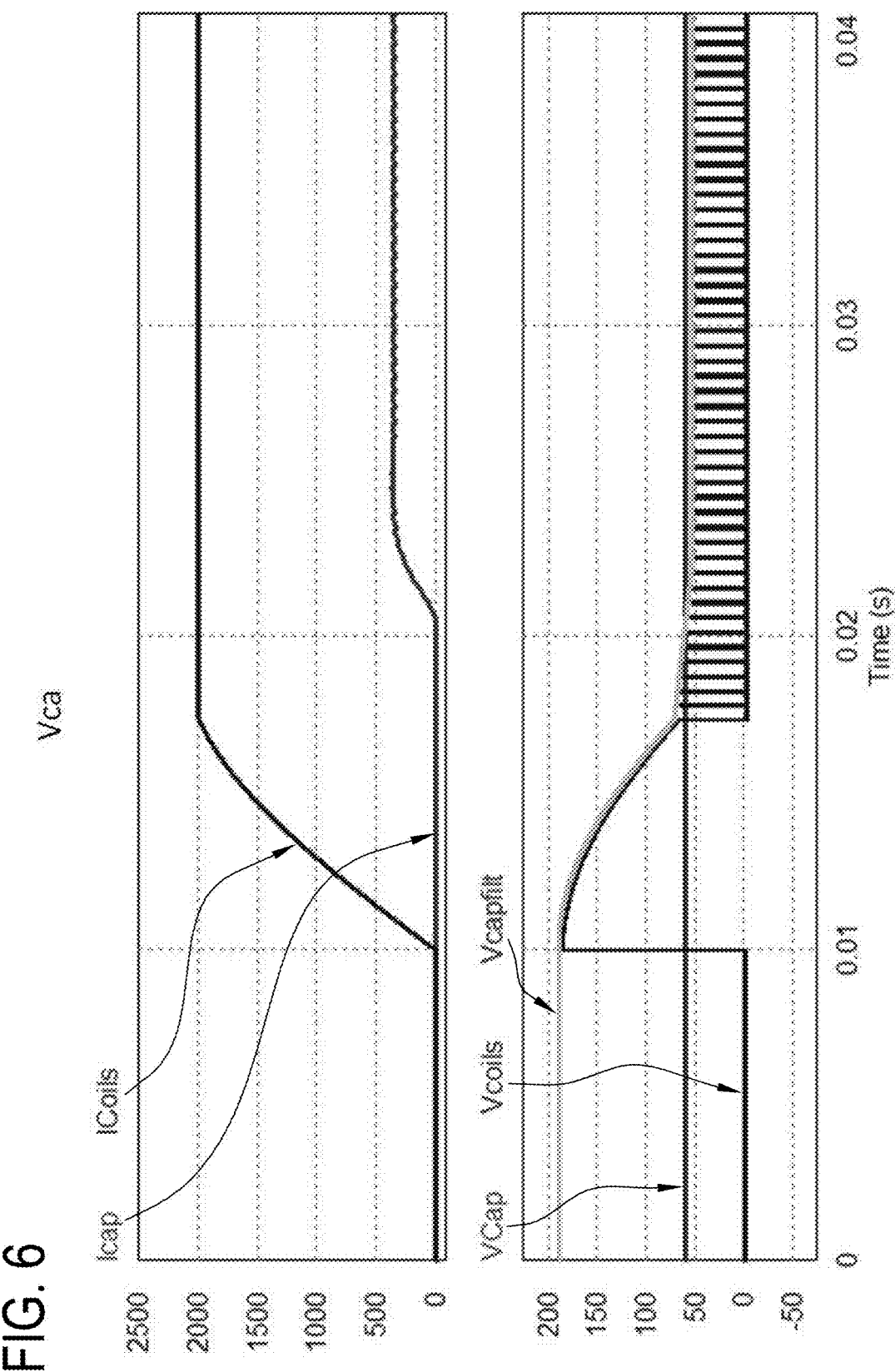
FIG. 6 illustrates in a diagram the start of a pulse (for a time of approximately 4 ms) in which the current starts to flow from the supercapacitors when VC1 drops below Vcap.
Figure 7:
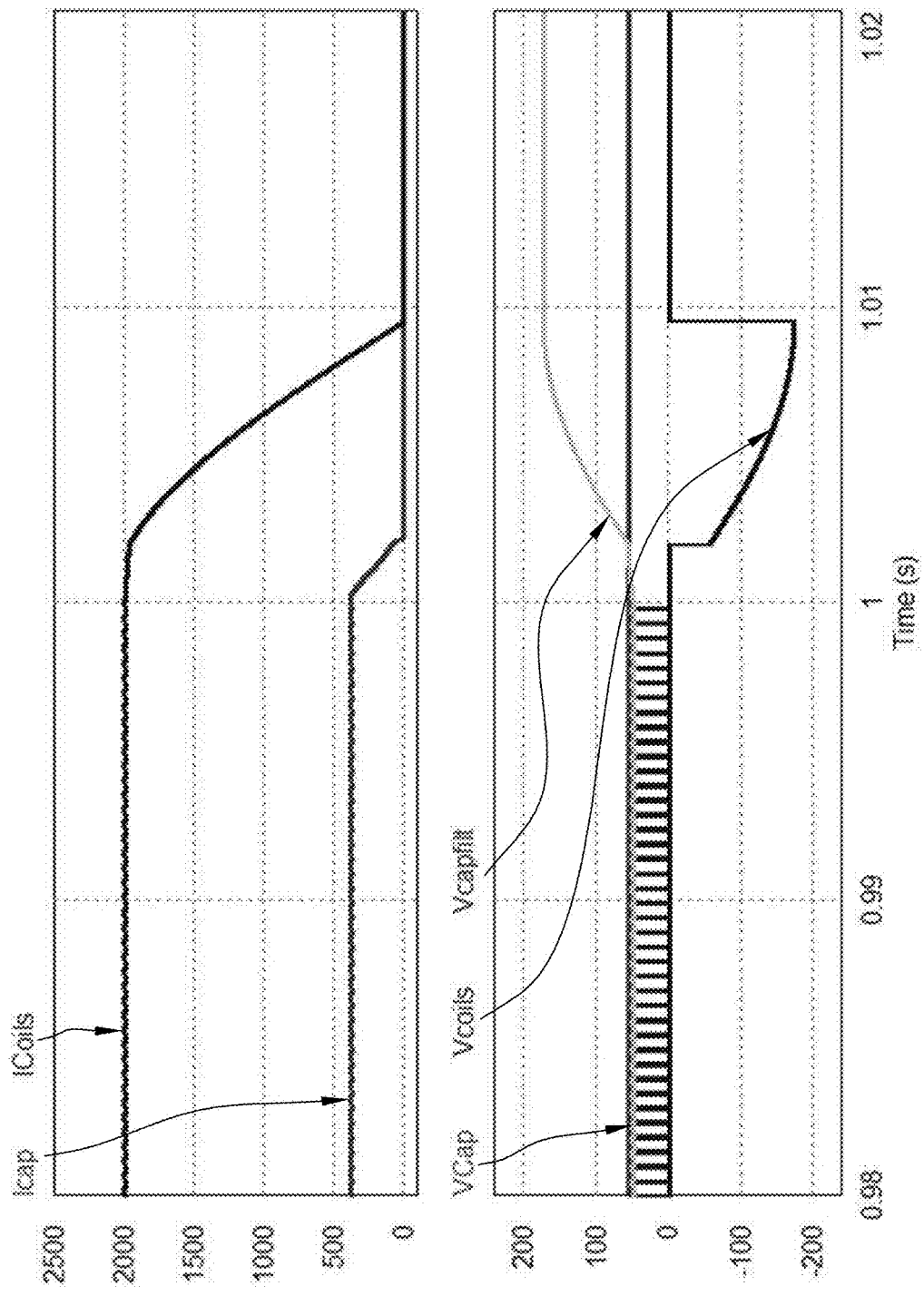
FIG. 7 illustrates in a diagram the end of a pulse, in which a voltage reduction on the supercapacitors is evident.

FIGS. 5, 6 and 7 denote: with Icap the current coming from the supercapacitor SC1 and which passes through L1; with Icoils the current I in the load RL; with Vcapfilt the voltage at the terminals of the capacitor C1; with Vcap the voltage at the terminals of the supercapacitors SC; with Vcoils the voltage Vc at the terminals of the load RL.

Figure 8:
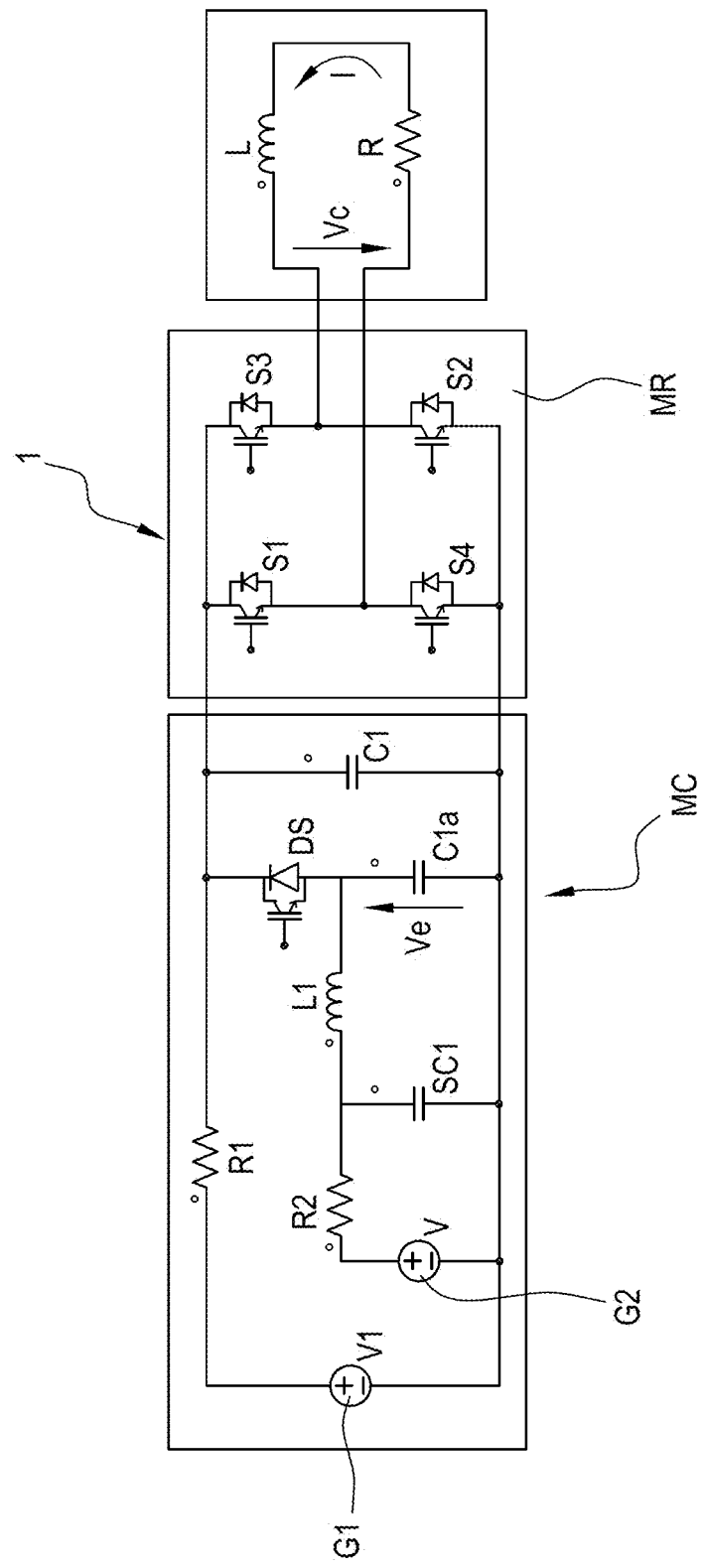
FIG. 8 illustrates a fourth configuration of the circuit of the generator according to this invention.

FIG. 8 illustrates a further embodiment of the electrical pulse generator.

It should be noted that, in this embodiment, the diodes D1 and D2 have been replaced by two IGBTs.

In this way, by suitably controlling the two IGBTs (activating/deactivating them) it is also possible to obtain the reversal of the current in the load LR.

The following should be noted with reference to the functionality of the capacitor C1.

This capacitor C1 performs a twofold function, that is to say: at the start and end of the pulse (when DS isolates it from SC), the capacitor C1 allows the creation of very high current derivatives; then, during the constant current phase with the diode DS in conduction, the capacitor C1 acts as a low-pass filter.

It should be noted that once the capacitor C1 has been discharged (that is, it has transferred its load), the capacitor C1 is to all intents and purposes in parallel with the supercapacitor SC1, contributing to the filtering of the alternating voltage/current component (which is generated by the regulating bridge MR).

For this reason, the capacitor C1, in a specific step, operates as a filter under voltage.

Figure 10:
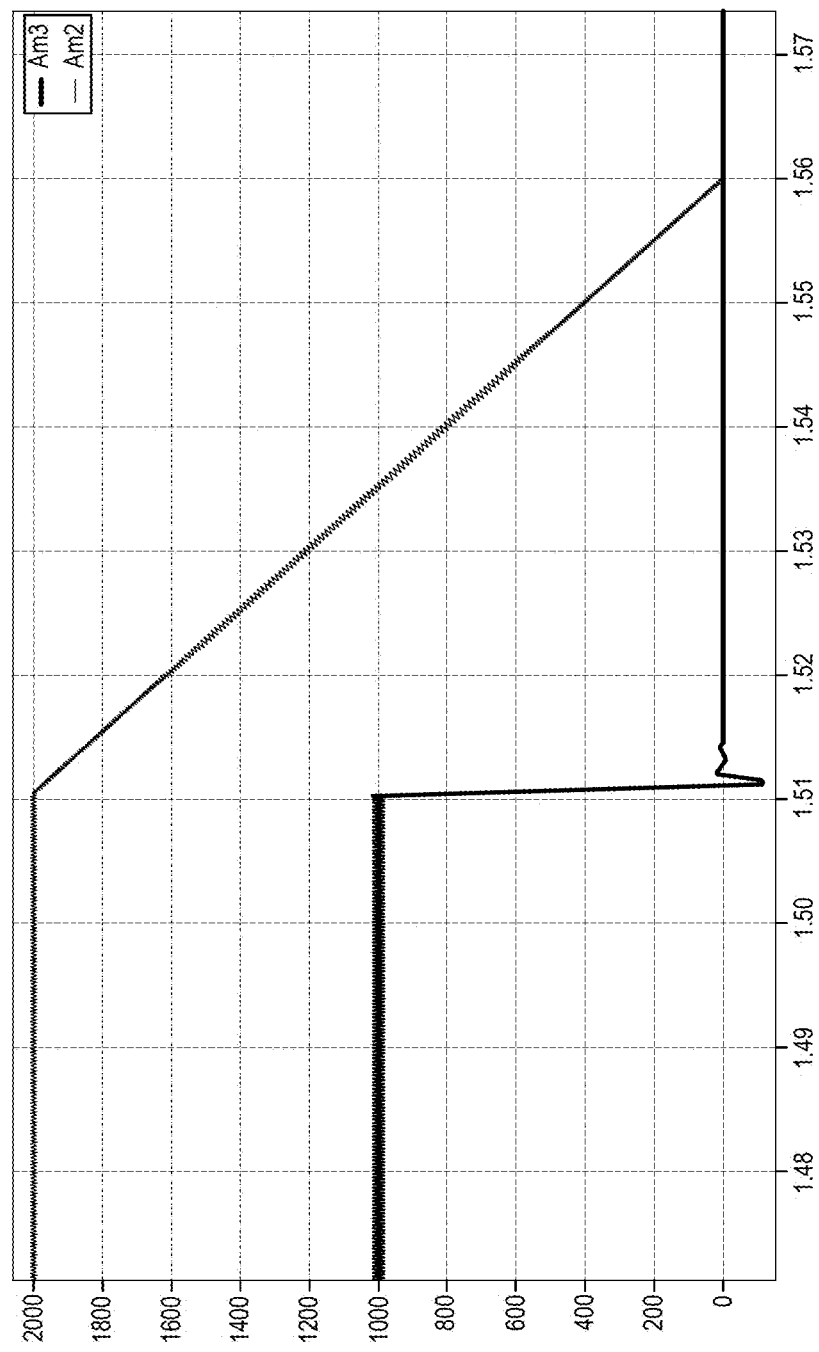
Figure 11:
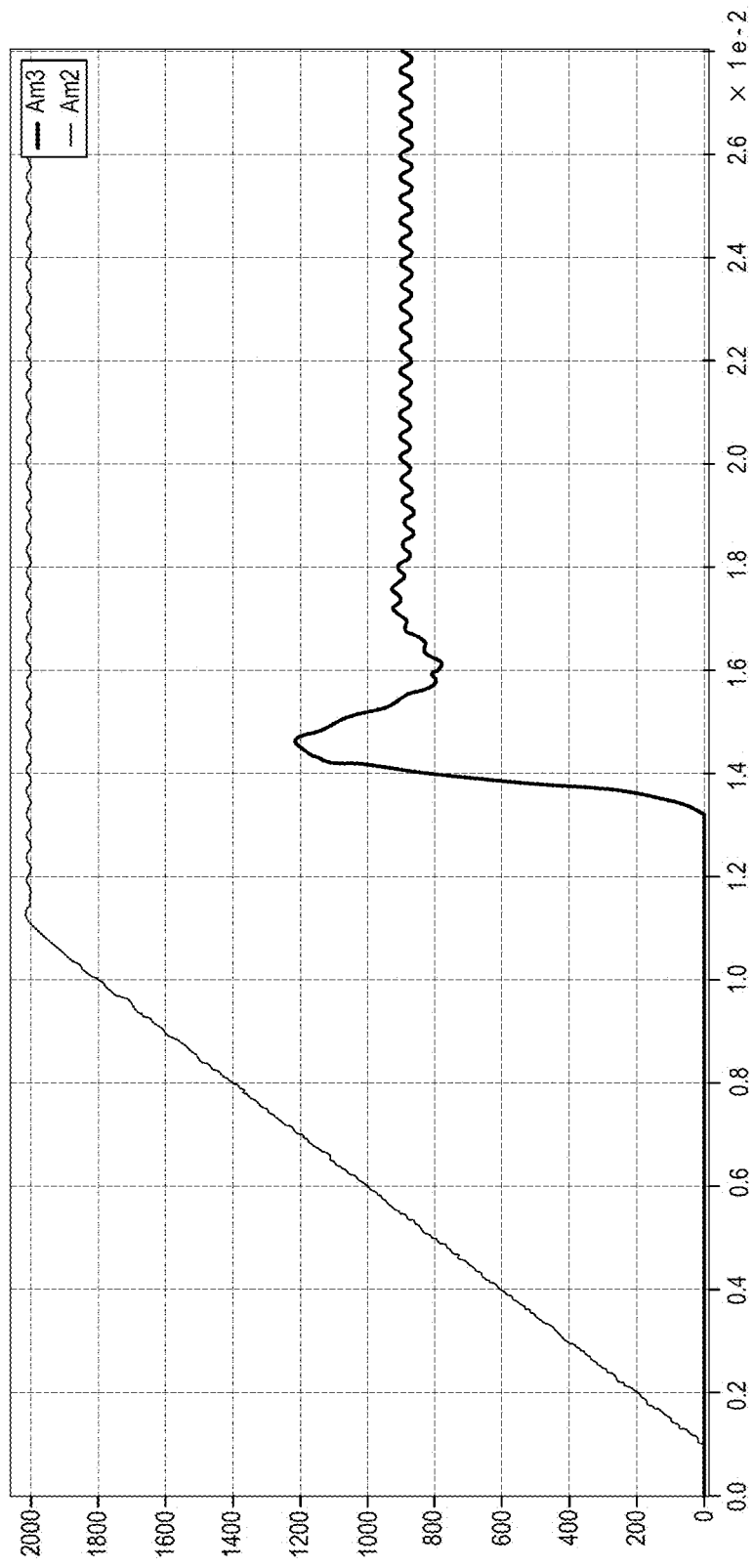

In this respect, it should also be noted that, at the end of the pulse, the switching off of the semiconductors S1 and S2 generates a rapid drop in the current (as shown in FIG. 10, curve am3) in the load LR.

Preferably, at the end of the pulse, in order to control the step of lowering the current in the load LR the semiconductors S1 and S2 are switched on (activated) for short intervals of time, during which the voltage on the load is thereby returned to values close to zero; this controls the average value of the voltage and therefore that of the derivative of the current in the load. In this way, the ramp of lowering the current in the load LR is controlled, that is to say, it is less steep.

According to another aspect, instead of the diodes Ds, D1 and D2 it is possible to use in the circuit according to the invention electronic components of the IGBT type: in this way, advantageously, it is also possible to recover the energy of the supercapacitors.

Figure 9:
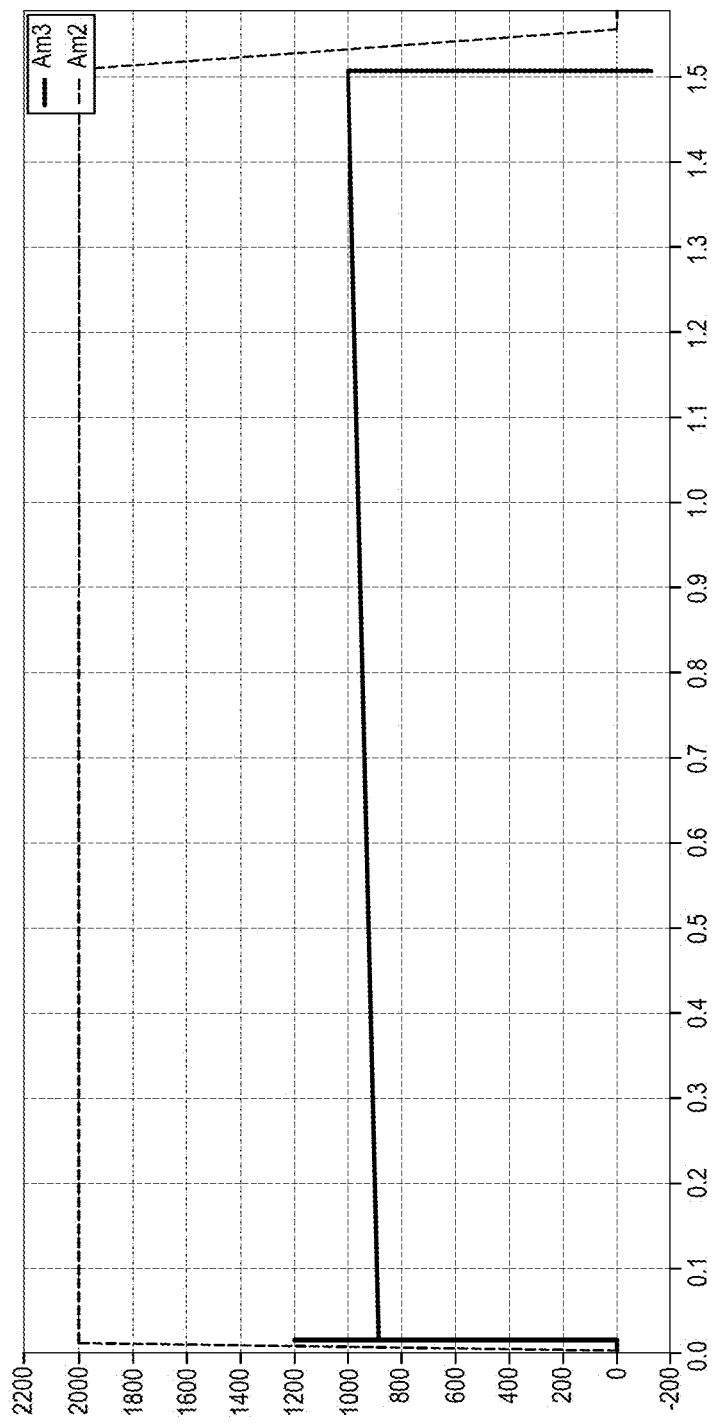
FIGS. 9 to 11 illustrate respective graphs relating to the electrical quantities over time measured in the circuit which forms part of the pulse generator according to this invention.

FIG. 9 illustrates, in a graph with current on the y-axis and time on the x-axis, the load current LR (curve am3) and the current in the supercapacitors SC1 (curve am2) in a period of time corresponding to before and after the switching off (deactivation) of the semiconductors S1 and S2.

FIG. 10 illustrates an enlarged view of a detail of FIG. 9, in particular the right-hand end part of the graph of FIG. 9.

FIG. 10 illustrates, in a graph with current on the y-axis and time on the x-axis, the load current LR (curve am2) and the current in the supercapacitors SC1 (curve am3) during an increase ramp.

Preferably, a diode (DS) and/or a semiconductor (e.g. IGBT) is interposed between the terminals (positive) of the primary (C1) and secondary (SC1) capacitor or capacitors.

Preferably, the diode (DS) and/or a semiconductor (e.g. IGBT) has the function of preventing the flow of current from the capacitor or from the primary capacitors (C1) towards the secondary capacitors (SC1).

The invention claimed is:

1. An electrical pulse generator for an ohmic-inductive load, comprising:
    a power supply module for supplying a first voltage V1 with pulses of duration Δt at terminals of the ohmic-inductive load, and a constant voltage Vc for maintaining a constant rated current I through the ohmic-inductive load for predetermined periods of time longer than the pulses of duration Δt,
    a capacitive module charged for supplying the first voltage V1 pulses and a constant operation voltage Ve higher than the constant voltage Vc necessary to circulate the current I through the ohmic-inductive load;
    a regulation module for splitting the constant operation voltage Ve supplied by the capacitive module according to high-frequency pulses,
    wherein the capacitive module comprises one or more primary capacitors for generating voltage pulses, with high voltage, charged by a first generator to the first voltage V1 to deliver energy to provide a voltage pulse having a corresponding voltage value; and
    wherein the capacitive module comprises one or more high capacity secondary capacitors, connected in parallel and charged by a second generator up to the constant operation voltage Ve, to provide voltage with continuity.

2. The electrical pulse generator according to claim 1, wherein the regulation module is configured to split the constant operation voltage Ve supplied by the capacitive module according to the high frequency pulses and an inversely variable duration based on the constant operation voltage Ve across terminals of the capacitive module.

3. The electrical pulse generator according to claim 2, and further comprising respective resistors decoupling the first and second generators from the respective one or more primary capacitors and the one or more secondary capacitors.

4. The electrical pulse generator according to claim 1, wherein the capacitive module is charged for supplying the first voltage V1 pulses and the constant operation voltage Ve higher than the constant voltage Vc necessary to circulate a substantially constant I current through the ohmic-inductive load.

5. The electrical pulse generator according to claim 4, and further comprising an LC low-pass filter for reducing or eliminating an alternated high-frequency component generated on the one or more secondary capacitors.

6. The electrical pulse generator according to claim 1, wherein the regulation module consists of a two quadrant electronic splitter, or chopper, which allows adjustment of a value of the constant operation voltage Ve supplied from the capacitive module.

7. The electrical pulse generator according to claim 6, wherein the two quadrant electronic splitter, or chopper, comprises two semiconductor switches and two diodes such that, when the two semiconductor switches are closed the power supply module can apply, due to a discharge of the one or more primary capacitors C1, a voltage pulse with duration Δt across the terminals of the ohmic-inductive load, thus raising the current I running across the ohmic-inductive load up to a predetermined value, at which the first voltage V1 across the terminals of the one or more primary capacitors is lower than the constant operation voltage Ve at the terminals of the one or more secondary capacitors which is supplied, at the end of time period of duration (Δt), to the two quadrant electronic splitter, or chopper, while the semiconductor switches are cyclically enabled and disabled to split the constant operation voltage Ve and keep constant the current I, with the diodes allowing, when the semiconductors are finally deactivated, the current I to reflow to the one or more primary capacitors, thereby recovering a portion of the energy previously delivered to the ohmic-inductive load.

8. The electrical pulse generator according to claim 7, wherein, when considering a relative inductance L for the ohmic-inductive load and a relative capacity C for the one or more primary capacitors and the one or more secondary capacitors with a corresponding voltage V, the following condition is validated:

$$C*V^2 > L*I^2$$

and also $$\Delta t \geq T/4 = \pi/2(L\ C)^{1/2}$$

from which it follows that $$C \leq (2\Delta t/\pi)^2/L$$

and $$V > (I)(L\ C)^{1/2}.$$

9. The electrical pulse generator according to claim 7, wherein a voltage VDRM of the semiconductor switches is lower than the first voltage V1 and further comprising:

a thyristor interposed between the power supply module and the two quadrant electronic splitter, or chopper, the thyristor being switched into conduction when the capacitive module must deliver current to the two quadrant electronic splitter, or chopper, and to the ohmic-inductive load, and an additional thyristor provided in parallel to the ohmic-inductive load and enabled into conduction when the current I must flow back from the ohmic-inductive load at the time when the semiconductor switches are opened and the first thyristor is disabled.

10. The electrical pulse generator according to claim 7, and further comprising a plurality of power supply modules which are connected to a plurality of two quadrant electronic splitters, or choppers respectively, the two or more two quadrant electronic splitters, or choppers being in turn connected in series and to the ohmic-inductive load.

11. The electrical pulse generator according to claim 1, and further comprising a diode interposed between positive terminals of at least one chosen from the one or more primary capacitors and the one or more secondary capacitors, the diode preventing the current I from flowing from the one or more primary capacitors to the one or more secondary capacitors.

12. The electrical pulse generator according to claim 1, wherein the capacitive module is contained in the power supply module and together with the regulation module are integrated in a single electronic circuit.

* * * * *